(12) United States Patent
Tang et al.

(10) Patent No.: US 10,681,923 B2
(45) Date of Patent: Jun. 16, 2020

(54) MICROWAVE STERILIZATION OR PASTEURIZATION TRANSPORT CARRIERS

(71) Applicant: Washington State University, Pullman, WA (US)

(72) Inventors: Juming Tang, Pullman, WA (US); Fang Liu, Pullman, WA (US)

(73) Assignee: Washington State University, Pullman, WA (US)

( * ) Notice: Subject to any disclaimer, the term of this patent is extended or adjusted under 35 U.S.C. 154(b) by 249 days.

(21) Appl. No.: 15/907,722

(22) Filed: Feb. 28, 2018

(65) Prior Publication Data

US 2018/0249736 A1 Sep. 6, 2018

Related U.S. Application Data

(60) Provisional application No. 62/467,018, filed on Mar. 3, 2017.

(51) Int. Cl.
| | |
|---|---|
| *A23L 3/01* | (2006.01) |
| *A23L 3/00* | (2006.01) |
| *H05B 6/78* | (2006.01) |
| *H05B 6/80* | (2006.01) |
| *A23L 3/04* | (2006.01) |
| *A61L 2/12* | (2006.01) |
| *A61L 2/26* | (2006.01) |

(52) U.S. Cl.
CPC ............... *A23L 3/01* (2013.01); *A23L 3/001* (2013.01); *A23L 3/04* (2013.01); *A61L 2/12* (2013.01); *H05B 6/782* (2013.01); *H05B 6/80* (2013.01); *A23V 2002/00* (2013.01); *A61L 2/26* (2013.01)

(58) Field of Classification Search
CPC ........... H05B 6/782; H05B 6/80; A23L 3/001; A23L 3/01; A23L 3/04; A61L 2/12; A61L 2/26; A23V 2002/00
USPC ......... 99/358, 378, 389, 390, 391, 392, 401, 99/447, 451, 646
See application file for complete search history.

(56) References Cited

U.S. PATENT DOCUMENTS

| | | | |
|---|---|---|---|
| 7,119,317 B2 | 10/2006 | Ando et al. | |
| 9,642,385 B2 | 5/2017 | Tang et al. | |
| 2005/0127068 A1 | 7/2005 | Tang et al. | |
| 2011/0281004 A1* | 11/2011 | Matsumoto | ............... A23L 3/04 426/399 |
| 2012/0012578 A1 | 1/2012 | Hach | |

(Continued)

*Primary Examiner* — Jermie E Cozart
(74) *Attorney, Agent, or Firm* — W&C IP

(57) ABSTRACT

An improved transport carrier for use in a fluid filled microwave sterilization or pasteurization system includes patterned electrically conductive layers or carriers which extend over or under items to be sterilized or pasteurized and occlude 1 to 30% of the area in the direct path of microwave emissions to the items. When the patterned electrically conductive layers or cages are present, heating of the items to be sterilized or pasteurized is substantially more uniform compared to when there is nothing occluding or otherwise interrupting the direct pathway from the microwave emitters to the items. Enhanced automation is achieved for sterilization or pasteurization systems by configuring the preheating and cooling sections as loading and unloading sections. Furthermore, superior fluid temperature control between the loading, heating, and unloading sections is achieved using double gates or dividers between sections.

18 Claims, 12 Drawing Sheets

(56) References Cited

U.S. PATENT DOCUMENTS

2016/0029685 A1 2/2016 Tang et al.
2017/0099704 A1 4/2017 Kimrey et al.
2018/0014559 A1 1/2018 Tang et al.

* cited by examiner

Top view

Side view

Front view

MICROWAVE STERILIZATION OR PASTEURIZATION TRANSPORT CARRIERS

CROSS-REFERENCE TO RELATED APPLICATIONS

This application claims priority to U.S. Provisional application 62/467,018 filed Mar. 3, 2017, and the complete contents thereof is herein incorporated by reference.

This invention was made with government support under 2016-68003-24840 awarded by the United States Department of Agriculture, under the National Institute of Food and Agriculture. The government has certain rights in this invention.

FIELD OF THE INVENTION

The present embodiments herein relate to microwave systems for heating one or more items, articles, and/or loads for purposes of sterilization or pasteurization. The present embodiments have particular application to food transport carriers for sterilizing or pasteurizing food products for later consumption by people or animals. More particularly, the transport carriers include electrically conductive, and preferably metallic or metal alloy, patterned portions which partially occlude a direct path from the microwave emitter to the items, articles, and/or loads to be sterilized or pasteurized. In addition, embodiments of the transport carriers function to fix and maintain the thickness of the pouches, trays, or other vessels which are placed in the transport carriers so that the pouches, trays, or other vessels do not expand or rupture whilst being heated with microwave energy. Furthermore, embodiments of the invention pertain to improved sterilization or pasteurization systems that utilize the transport carriers.

BACKGROUND OF THE INVENTION

Discussion of the Related Art

Sterilization or pasteurization has been used in preserving foods, preventing sepsis in humans and animals, and in other fields. For example, food products can be sterilized or pasteurized to reduce or eliminate fungi, bacteria, viruses, spore forms, or other harmful microbiological organisms that may cause spoilage or even food-borne diseases. One sterilization or pasteurization technique includes heating food products with hot air, hot water, or steam. Heating in such a manner, however, can result in poor taste, texture, color, or smell of the food products. Also, such heating techniques can be energy inefficient and may require long processing times.

The applicants have worked for a number of years on developing microwave sterilization and/or pasteurization systems which overcome the deficiencies described above. In U.S. Pat. No. 7,119,317 to Tang et al., the basic concept of microwave heating of food products in a water filled passage is described. Trays are not used in U.S. Pat. No. 7,119,317. Rather, individual food products are affixed to pulleys and are moved in and out of locations where the food products are exposed to microwave energy. In U.S. Pat. No. 8,981,270 to Tang et al., positioning of a temperature probe within a package which is subjected to microwave heating is described. In U.S. Pat. No. 9,642,385 to Tang et al. the following basic concepts are described: (1) having a plurality of individual food products (e.g., separate pouches or containers) on a transport carrier which is passed through a microwave heating device, (2) having multiple transport carriers passing through a system with pre-heating and cool down circuits, where the transport carriers individually pass through a heating section where the food products on the transport carriers are subjected to heating by circulating water and microwave energy, and (3) using the height of the pre-heating section of the system to apply hydrostatic pressure to packaged food products on the transport carriers such that heating of the food products by exposure to microwave energy does not cause bursting of the packages. In U.S. Pat. No. 9,642,385 to Tang et al., the transport carriers or portions thereof may be made of metal, and teaches that the transport carrier configuration can influence the microwave heating profile of the food products on the transport carrier. U.S. Pat. No. 9,642,385 to Tang et al. also describes the possibility of having different sized products on the same transport carrier or different sized products on different carriers. In PCT/US2017/042546 to Tang et al. describe the ability to have more uniform cooking be achieved when using metal transport carriers. The PCT/US2017/042546 embodiments include having transport carriers configured to have different sized openings to accommodate different sized pouches. Clips at the edges of openings in the transport carriers are used to secure pouches in the openings of the transport carriers.

U.S. Patent Publication 2017/0099704 to Kimrey describes a conveyor line carrier used in a microwave heating system. The carrier is constructed from a low loss tangent material such as polymers (e.g., polytetrafluoroethylene (PTFE), polysulfone, etc.) with spaced apart support upper and lower support structures configured from a plurality of parallel slats that extend between ends of the carrier. Items to be exposed to microwave radiation are positioned between the support structures. The slats themselves include electrically conductive material, and Kimrey suggests the parallel electrically conductive slats can increase uniformity of microwave heating.

Despite the many advances developed by the applicants, there is still a need for improving the uniformity of heating and control of heating for food products and other items, articles, and/or loads that are to be sterilized or pasteurized. It would be advantageous to be able to reliably and controllably produce multiple sterilized or pasteurized items, article, and/or loads that are each uniformly heated and that are each heated to substantially the same degree as every other item, article, and/or load. For example, if hundreds to thousands of packages of mashed potatoes, peas, chicken, fish, beef, rice, surimi, or other food product of interest are produced, it would be advantageous to have a system where each of the packages are uniformly pasteurized or sterilized with relatively few cold or hot zones within each package, and where each of the packages are pasteurized or sterilized to approximately the same degree (i.e., different packages are heated approximately the same amount, e.g., less than 5% variation from package to package and most preferably less than 1% variation from package to package).

SUMMARY OF THE INVENTION

Applicants have determined that partially occluding or otherwise interrupting the pathway between microwave emission sources, and items, articles, and/or loads to be sterilized or pasteurized, with patterned electrically conductive cages or layers, can dramatically improve the uniformity in which the items, articles, and/or loads are heated by microwaves in all metal transport carriers. The amount of occlusion required to achieve the improved heating first observed by the applicants is relatively small, e.g., 1-30%, and more preferably 1-20%, 5-20%, 1-15%, 5-15%, 1-10%, or 5-10%. The type of pattern can vary widely, e.g., bars, cages, X's, circles, letters, random, etc. Very good results were obtained with a cage design prepared based loosely on the concept of a Farraday cage where portions of the pattern extend in parallel to opposite sides of a location where an item to be sterilized or pasteurized is positioned, and portions of the pattern extend vertically to opposite edges of the same location. Experiments below demonstrate the invention provides substantial benefits for uniform heating of food items, such as mashed potatoes, peas, chicken, fish, beef, rice, surimi, etc., when compared to microwave heating when no occlusion of the direct path from a microwave emission source to the food item is present. Uniform heating may also be obtained with mixtures of food items, e.g., broccoli, beef, and chicken, etc. Furthermore, the microwave transport carriers of this invention may be used with any item requiring sterilization or pasteurization by microwave energy, e.g., medical supplies and materials, dental instruments, pharmaceuticals, etc.

In some embodiments, the invention includes a transport carrier for carrying one or more items to be sterilized or pasteurized by microwave emissions, which includes both a carrier base transportable through a fluid filled microwave heating zone, and one or more patterned electrically conductive cages or layers which fit on or within the carrier base and over and/or under the one or more items to be sterilized. In various embodiments, the electrically conductive cages or layers or constructed from or contain metal or metal alloy materials. While the items to be sterilized or pasteurized are partially occluded from a direct path from the microwave emissions source, the metal or metal alloy materials do not prevent proper heating of the items by microwave emissions as might be expected. Rather, the patterned conductive cages or layers have been shown to enhance the speed and uniformity of heating the items. In addition, in embodiments where the cages or layers are held to the carrier base, they effectively set a predetermined fixed thickness for pouches or other containers which contain the items to be sterilized or pasteurized, thereby preventing expansion or bursting of the packaging while it is subjected to microwave heating and also ensuring a more uniform heating of the items within the packaging.

Preferably, the carrier base is rectangular, and has opposing first and second sides and opposing first and second ends which define a space in the carrier base where one or a plurality of items to be sterilized or pasteurized are positionable at one or a plurality of locations within the space. The carrier base has a top and a bottom, and the space in the carrier base where the one or the plurality of items to be sterilized or pasteurized are positionable is configured to be exposed from either or both the top and the bottom of the carrier base. This allows microwave emissions to contact or penetrate the one or the plurality of items to be positioned in the space from above and/or below the carrier base. Each of the one or the plurality of locations define an area of microwave emission exposure from above and/or below the carrier base. That is, the one or the plurality of items to be positioned at the one or the plurality of locations are exposed to microwave emissions at each area. One or more patterned electrically conductive cages or layers are configured to fit within the space defined by the opposing first and second sides and the first and second ends of the carrier base. In preferred embodiments, two patterned electrically conductive layers are positionable in the carrier base above and below the one or more items to be sterilized or pasteurized and define a fixed space therebetween which prevents unintended overexpansion of packaging during heating. In other embodiments, a single electrically conductive layer can be positioned above (i.e., over) or below (i.e., under) the packages between the microwave emission source and the packaged items. The one or more patterned electrically conductive cages or layers are sized so as to interrupt microwave emissions emitted directly from one or more microwave emission sources above and/or below the carrier base over 1-30% of the area of exposure defined by each of the one or the plurality of locations. That is, the direct pathway from the microwave emission source to each item being sterilized or pasteurized is occluded or otherwise interrupted by the electrically conductive pattern or cage. The electrically conductive pattern or cage in some embodiments is or contains metal or metal alloy. The applicants have surprisingly found that this interruption in the direct pathway yields a more uniform, and possibly quicker, heating of the items to be sterilized or pasteurized, as compared to prior transport carrier configurations which do not have a pattern or cage of or containing electrically conductive materials between the microwave emission source and the items being sterilized or pasteurized, particularly when the carrier base and dividers which divide each of the plurality of locations within the carrier base for items to be sterilized or pasteurized are also made of metal or metal alloy. The all metal construction of the carrier base and patterns or cages provide benefits in transfer of energy from, e.g., a 915 MHz microwave sources to, e.g., food products, at the specific locations in the carrier base, as well as in durability for continuous production of hundreds to thousands of sterilized or pasteurized items.

DETAILED DESCRIPTION

Embodiments of this invention are directed to transport carriers used to transport one or a plurality of items, articles, and/or loads through a fluid filled sterilization or pasteurization system where the items, articles, and/or loads are subjected to microwave heating to achieve sterilization or pasteurization. The invention has particular application for sterilizing and pasteurizing food products, e.g., mashed potatoes, peas, chicken, fish, beef, rice, surimi, etc., and this application will describe sterilization and pasteurization of food products as an example application. However, it will be recognized that embodiments of the invention can be used for sterilization or pasteurization of any item in need of such treatment, e.g., medicines, medical materials, dental instruments, pharmaceuticals, etc. Exemplary sterilization or pasteurization systems in which embodiments of the invention can be employed are described in U.S. Pat. No. 9,642,385 to Tang et al. and PCT/US2017/042546 to Tang et al., both of which are herein incorporated by reference.

Figure 1:
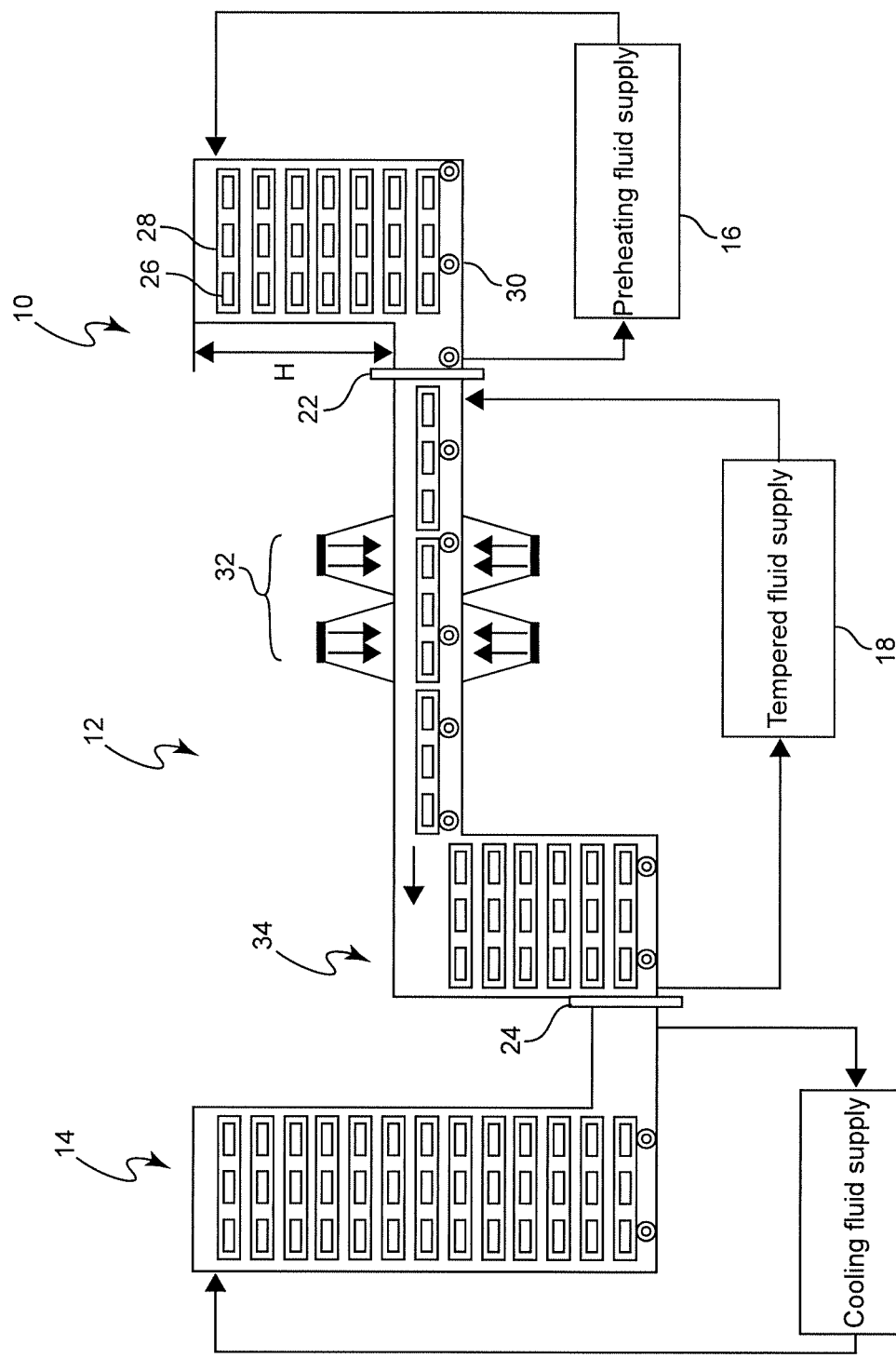
FIG. 1 is a schematic diagram illustrating a processing system useful for sterilization or pasteurization in accordance with embodiments of the disclosed technology.

FIG. 1 appears in both of the above-identified Tang references and shows an exemplary sterilization or pasteurization system in which the novel transport carriers can be used, wherein the sterilization or pasteurization system is divided into a preheating section 10, microwave heating section 12, and cooling section 14. Each of these sections can have its own temperature controlled fluid supply 16, 18, and 20, which circulates heated fluid, which is preferably heated water, to maintain the temperature in the respective sections at a desired level. The temperature in the heating section 12 is preferably warmer than the temperature in either the preheating section 10 or cooling section 14. Preferably, the water level in either or both the preheating section 10 or cooling section is a height H above the top of the heating section 12. This applies hydrostatic pressure to packages while they are being heated in the heating section, thereby allowing higher temperatures to be reached while microwave heating and helps prevent the packaging material from bursting. Gates or dividers 22 and 24 separate the three sections so that the temperatures of each of the sections can be separately controlled. A plurality of transport carriers 26 can be loaded into the preheating section 10, where, with time, the temperature of all of the items 28 on each of the transport carriers reach approximately the same temperature (e.g., they are homogenized to approximately the same temperature of the fluid circulated in the preheating section). Thus, upon entry into the heating section 12, the temperature of the items 28 on each of the transport carriers 26 will be approximately the same. Entry into the heating section 12 is controlled by briefly opening divider 22, and transporting the carriers one at a time into the heating section 12 using rollers 30 or other conveying mechanisms (e.g. a conveyer belt, etc.). In the heating section 12, the transport carriers 26 pass under and/or over one or more microwave emission stations 32 where the items 28 on the carriers 26 are heated by exposure to microwaves. As explained in the above-identified Tang references, microwaves at 915 MHz penetrate deeply in tap and deionized water, in particular at elevated temperatures (for example, >150 mm at 120° C.). Thus, in preferred embodiments the transport carriers of the present invention are transported through a water filled heating section 12 including one or more microwave emission stations 32 that expose the items on the carriers 26 to microwaves at 915 MHz. The direction of exposure can be from above and below the carriers 26 as shown in FIG. 1; however, in some applications microwave energy exposure may only be from the top or only from the bottom. Similarly, while FIG. 1 shows simultaneous exposure from above and below the items 28, exposure could be sequentially, e.g., from above, then from below, etc. In addition, exposure to microwaves may occur while the items 28 are being transported past the microwave emission stations 32, or the transport carriers 26 might be halted briefly under the microwave emission stations 32 for a time suitable for sterilization or pasteurization of the items 28. After being exposed to microwaves for the requisite amount of time, the transport carriers 26 may be moved to a holding area 34 in the system and then through divider 24 in the cooling section 14 of the sterilization or pasteurization system.

Figure 2:
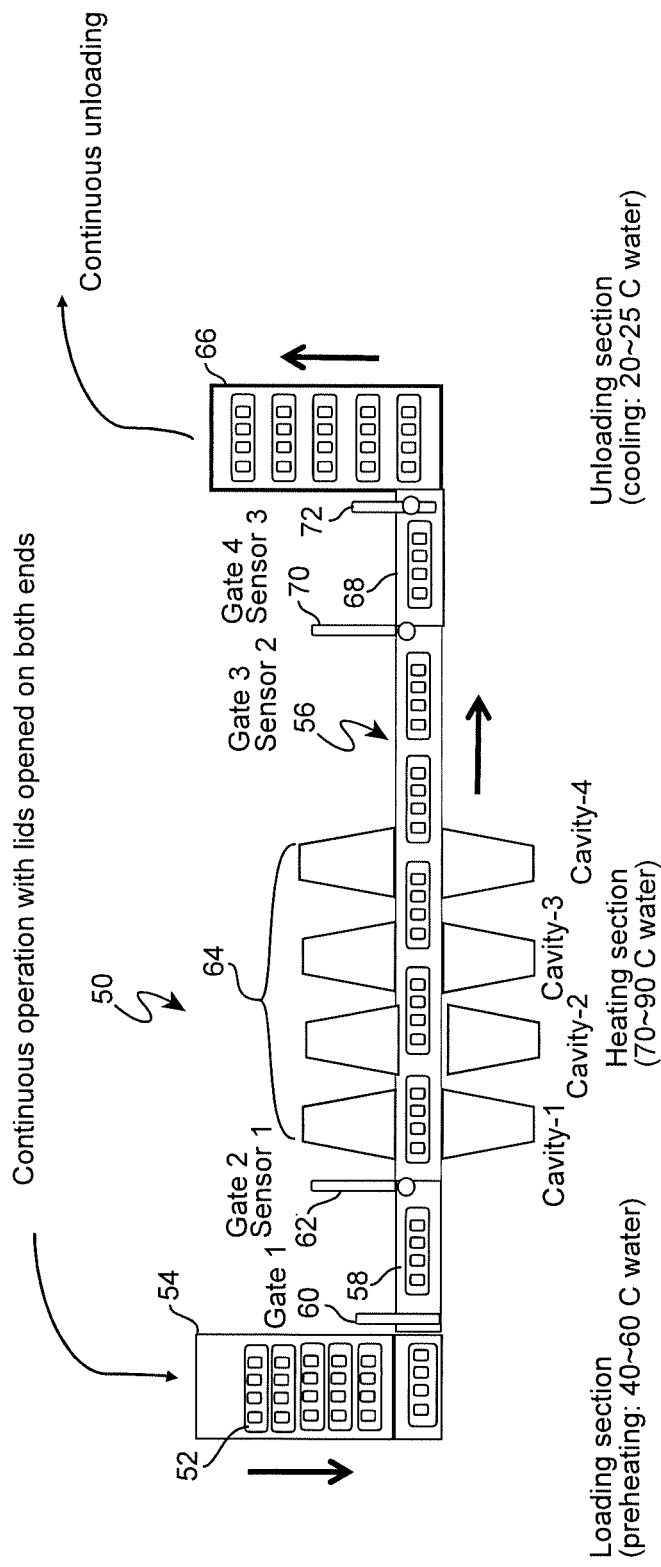
FIG. 2 is a schematic diagram illustrating another processing system useful sterilization and pasteurization in accordance with embodiments of the disclosed technology.

FIG. 2 shows an alternative sterilization or pasteurization system 50 in which embodiments of the transport carriers 52 according to this invention may be employed. Alternative sterilization or pasteurization system 50 includes some refinements over the earlier system described in the two above-identified Tang references and the system constitutes part of the invention set forth in this application. The sterilization or pasteurization system 50 has the advantage of allowing for continuous operation wherein transport carriers may be vertically stacked in a loading section 54 which functions as a fluid filled preheating section (as discussed in conjunction with FIG. 1). Stacking may be easily achieved through an opening in the top of the loading section 54 or at a side of the loading section above the water line. As with FIG. 1, the water line of the preheating section and/or cooling section is preferably at a height above the top of the heating section so as to allow the application of hydrostatic pressure to the packages during microwave heating.

When being transported from the loading section 54 to the heating section 56, the individual transport carriers 52 pass through a passage 58 defined by gates or dividers 60 and 62, particularly, when the divider 60 closes after a transport carrier passes through and before divider 62 is opened. This double divider can function much like a restaurant vestibule which protects diners from the cold outdoor environment while dining.

In the heating section 56, the transport carriers 52 pass through a microwave heating area 64 which includes one or more microwave emission stations. In FIG. 2, four microwave emission stations above the heating section 56 and four microwave emission stations below the heating section 56 are employed. As discussed above in conjunction with FIG. 1, the microwave emissions are preferably at 915 MHz. The intensity and/or duration of exposure of items on a transport carrier 52 at each microwave emission station may be the same or different. As discussed above in conjunction with FIG. 1, in some embodiments, there may not be microwave emission stations both above or below the heating section, and, in some embodiments, the heating from above and below may be sequential instead of simultaneous. Furthermore, the transport carriers 52 may pass continuously through the heating section 56 or be stopped briefly at one or more microwave heating stations.

Before the transport carriers 52 reach the unloading section 66, they preferably pass through a double gate or divider passage area 68 similar to passage 58. In some embodiments, divider 70 will close after a transport carrier 52 reaches the passage area 68, and, after closure of divider 70, divider 72 will open. In this way the temperature of fluid (e.g., water) in the heating section 56, and the temperature of the fluid (e.g., water) in the unloading section 66 can better maintained. The unloading section 66 functions like a cooling section as discussed in conjunction with FIG. 1. Unloading of transport carriers 52 carrying items which have been sterilized of pasteurized using microwave energy can be easily accomplished by removing them through an opening in the top of the unloading section 66 or an opening in the side of the unloading section 66 above the water line.

Similar to that described in conjunction with FIG. 1, the preheating is performed preferably by circulating fluid in the loading section 54, the heating is performed by circulating fluid in the heating section 56 as well as by microwave exposure, and the cooling is preferably performed by circulating fluid in the unloading section 66. The circulating fluid (e.g., heated water) in the sterilization or pasteurization system 50 of FIG. 2 is preferably at different temperatures in the loading/heating section 54, heating section 56, and unloading/cooling section 66. For example, in some embodiments, the loading section 54 may be maintained at about 40-60° C., the heating section may be maintained at about 70-90° C. (e.g., at or near the temperature required for sterilization or pasteurization), and the unloading section 66 may be maintained at about 20-25° C. The duration of time the transport carriers 52 spend in the unloading section 54, heating section 56, and loading section 66 may vary depending on the application. A particular advantage of the sterilization or pasteurization system 50 is that it can be automated to continuously take in a plurality of transport carriers 52 and output a plurality of transport carriers 52. Thus, the sterilization or pasteurization system 50 allows for, e.g., continuous production of sterilized or pasteurized food products, etc. In the loading section 54 and/or unloading section 66, a plurality of trays are stacked and moved vertically. The transit time in the loading section 54, from top to bottom, assures that the packages on each of the different transport carriers 52 is substantially the same before the transport carrier is moved into the heating section for heating by the warmed fluid in the heating section and the microwave energy (e.g., 915 MHz).

Figure 3:
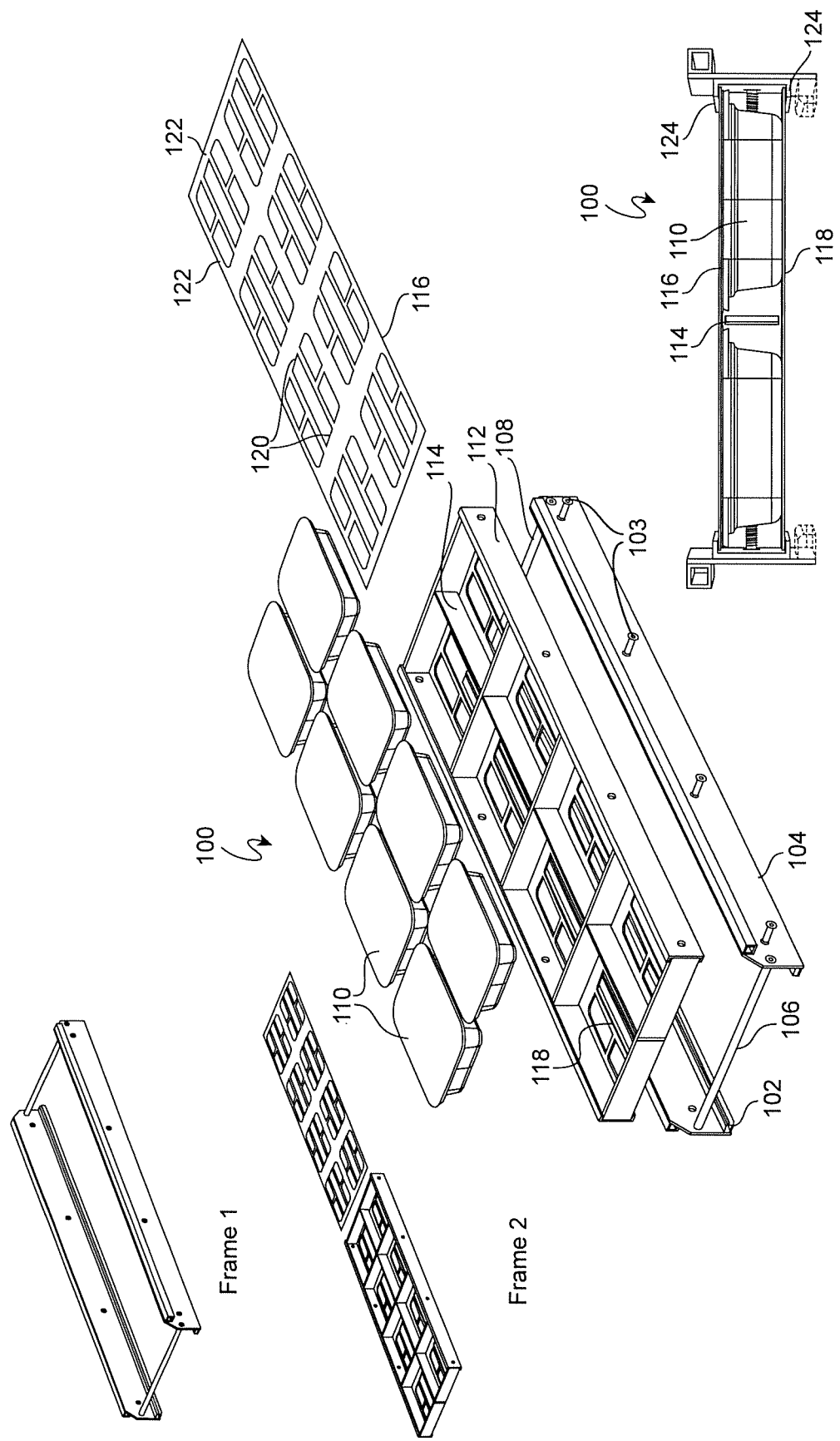
FIG. 3 is an exploded view and front view of an embodiment of a transport carrier according to the present invention.

FIG. 3 depicts an embodiment of a transport carrier 100 according to the invention. The transport carrier 100 is configured to be transported through a sterilization or pasteurization system such as those described in FIGS. 1 and 2. The carrier 100 has opposing side walls 102 and 104 which are connected at first and second ends 106 and 108 to form a carrier base which has an open space for one or a plurality of items 110 to be positioned for microwave sterilization or pasteurization. In the embodiment of FIG. 3, the carrier base is configured to receive an inner frame 112 which has inner walls 114 which define several locations where individual items 110 are to be positioned. The inner walls 114 may be configured to accommodate several items 110 that are the same size, and also may be configured to accommodate items that are of different sizes. The inner frame 112 and the inner walls define an area where the individual items 110 will be exposed to microwave energy. In the configuration presented in FIG. 3, exposure will be from both above and below the transport carrier 100; however, as discussed above, in some applications exposure may only be from above or only be from below the transport carrier. The inner frame 112 may be secured to the opposing side walls 102 and 104 by a plurality of screws 103 or other suitable fastening elements.

There are patterned layers 116 and 118 which are positioned above and below the items 110. The patterns 120 on the patterned layers 116 and 118 are configured to occlude or otherwise interrupt a direct path from microwave emitter sources above and below the carriers over 1-30% of the area defined by the locations which hold each of the items 110. This percentage of occlusion or interruption excludes regions 122 of the patterned layers 116 and 118 which do not extend over the locations for the items 110, e.g., portions of the patterned layers 116 and 118 which are at the ends or which are configured to be over the inner walls 114, etc. While FIG. 3 shows the patterned layers 116 and 118 are patterned with identical patterns 120, in some embodiments the patterns 120 on each layer 116 and 118 do not need to be the same. Furthermore, the individual patterns 120 on a single layer 116 or 118 do not need to be the same.

The cross-sectional view in FIG. 3 shows that the top and bottom patterned layers layer 116 and 118 may be fit under and over inward projecting flanges 124 with the inner frame 114 and items 110 therebetween. In this configuration, the amount of expansion of the items 110 under microwave heating is fixed. That is, the packaging of the items 110 is prevented from bursting as the items 110 are heated, and the thickness of the items is maintained during heating thereby providing better uniformity in heating throughout the items.

In the practice of the invention, the patterned layers 116 or 118, or, alternatively individual cages fitting over the items 110, either include or are made from electrically conductive materials, e.g., metal or metal alloys. While not to be bound by theory, the patterned layers 116 and/or 118 may function somewhat like a Faraday cage. However, the patterned layers 116 and/or 118 do not protect the underlying from item from electromagnetic radiation. Rather, as will be shown by test results below, the occluding or interrupting pattern results in a more uniform heating by microwaves whether by diffraction, reflection, and/or other means. Preferably, the inner frame 112, inner walls, and/or opposing side walls 102 and 104 are also made from or include electrically conductive materials, e.g., metals or metal alloys. The configuration positions the items 110 at individual locations surrounded by one or more electrically conductive elements (e.g., patterns 120, walls 114, frame 112, sidewalls 102 and 104). Exposure of the items 110 to microwave emissions from above and/or below carrier 100 is demonstrated herein to result in superior uniformity of heating (e.g., less cold spots or hot spots in food items, etc.) and possibly quicker heating for sterilization or pasteurization purposes when the patterns extend over part of the area of exposure.

The electrically conductive pattern to be positioned over the items to be sterilized or pasteurized can vary depending on the application and/or desires of the fabricator. At least some of the area of exposure must be occluded or interrupted from a direct path from microwave emissions, but not too much otherwise heating would be impaired via blocking of the microwave emissions. For example, the percentage of direct path occlusion or interruption should be 1-30%, and more preferably 1-20%, 5-20%, 1-15%, 5-15%, 1-10%, or 5-10%. Several exemplary variations on electrically conductive patterns which may be employed in the practice of the invention are discussed below in connection with FIGS. 5B-C.

Figure 4A:
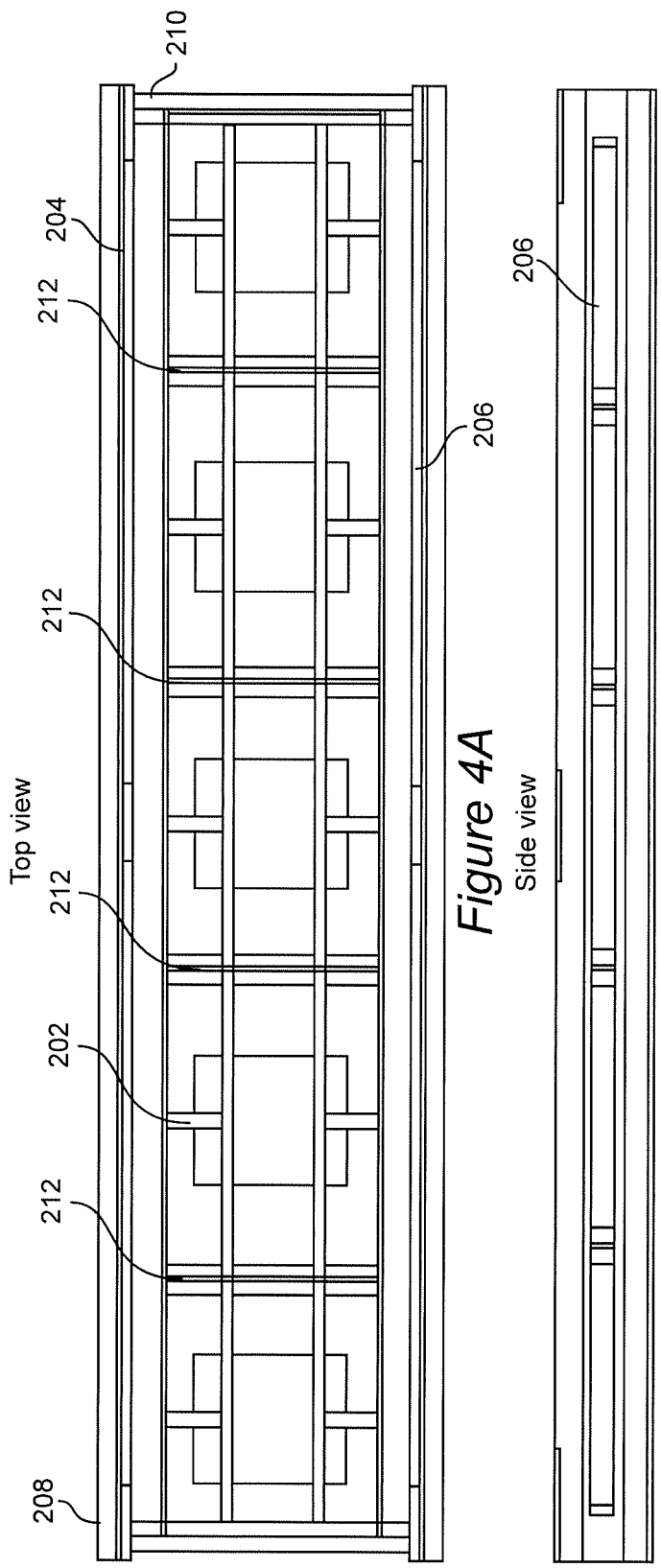
FIG. 4A-C a respectively top, side, and front views of an embodiment of a transport carrier according to the present invention.
Figure 4B:
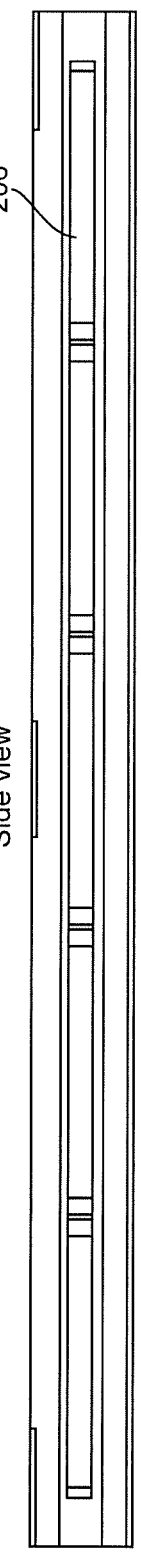
Figure 4C:
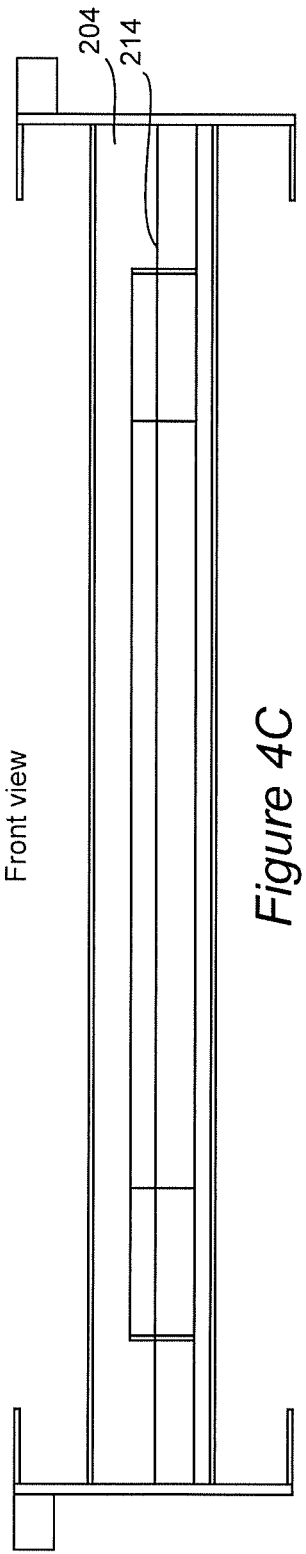

FIGS. 4A-C shows a transport carrier 200 similar to that described in conjunction with FIG. 3. In particular, in FIG. 4A, a patterned layer 202 is positioned in the space created by the opposing side walls 204 and 206 and front and back ends 208 and 210. Rather than having an internal frame, as described in conjunction with FIG. 3, FIG. 4a shows a plurality of electrically conductive straps 212, e.g., metal straps, which may extend between the opposing side walls 204 and 206 or to a frame which is secured to the opposing side walls 204 and 206. The straps 212 define locations for individual items to be placed in the transport carrier 200 for sterilization and pasteurization. The straps 212 help contain the items at the different locations in the transport carrier 200 as the transport carrier traverses through the sterilization or pasteurization system, and may reflect microwave energy towards the items being sterilized or pasteurized. The transport carrier 200 in FIG. 4A is constructed for large items than the transport carrier 100 in FIG. 3, as there are four locations for items, e.g., food pouches or containers, as opposed to eight. The number of locations and the size for those locations in the transport carrier 200 can vary widely depending on the application. FIG. 4B shows the sidewall 206 can have a sloped front end as a matter of designed choice. FIG. 4C shows an inward projecting top flange 214 on sidewall 204. Similar to FIG. 3, patterned electrically conductive layers 202, may be held in place over items to be sterilized or pasteurized, by sliding them under a top flange and over the items, and over a bottom flange and under the items, thereby holding the items in place between the top and bottom patterned electrically conductive layers and separated by the straps.

Figure 5A:
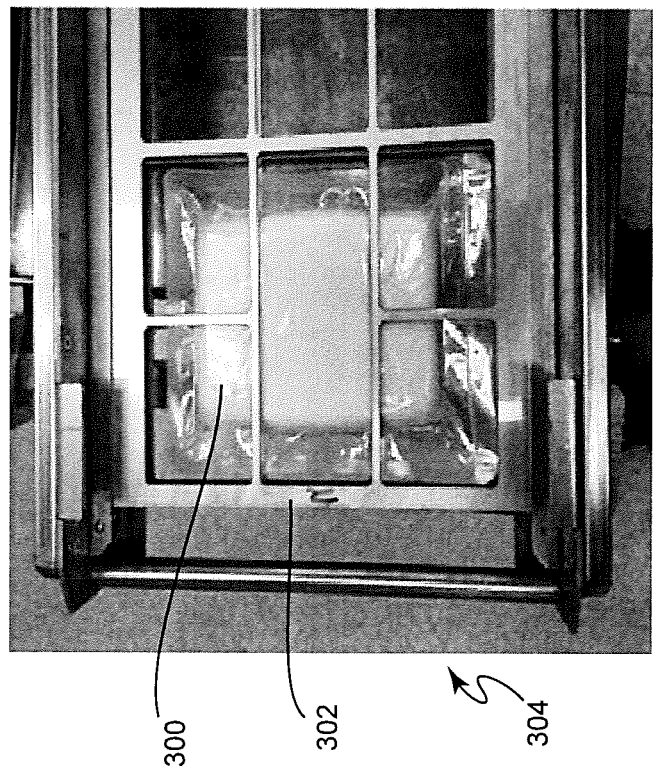
FIG. 5A is an enlarged top view of one end of the transport carrier shown in FIG. 4A-C showing a pouch positioned in a location at the end of the carrier between top and bottom patterned layers.

FIG. 5A shows a pouch 300 containing an item to be sterilized or pasteurized which is sandwiched between an upper electrically patterned layer 302 and a lower electrically patterned layer (not shown). As can be seen from FIG. 5A, the area which receives microwave emissions is occluded or otherwise from the top by the pattern covering 1-30% of the area directly exposed to emissions from a top mounted microwave emissions source. The transport carrier 304 housing the pouch 300 is transported through a sterilization or pasteurization system, such as that shown in FIG. 1 or 2.

Figure 5B:
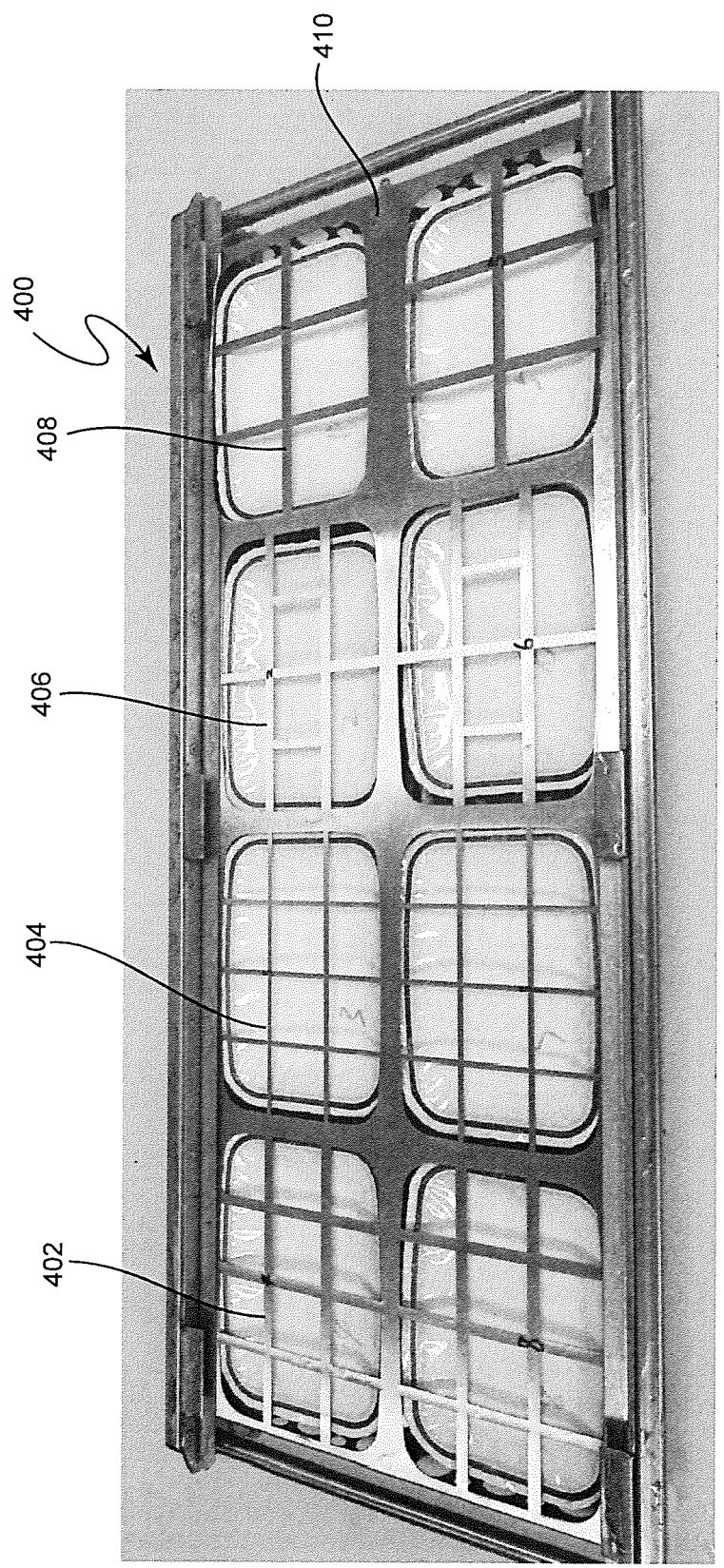
FIG. 5B is a top view of a transport carrier with different electrically conductive patterns (e.g., metal or metal alloy) at each of eight locations where, for example, eight 10.5 Oz food pouches or trays may be located.

FIG. 5B shows a transport carrier 400 wherein a food pouch is present at each of eight locations on the transport carrier 400. The patterns 402, 404, 406, and 408 are at openings in the conductive layer 410 which will be positioned at each food pouch or container location where the food (or other item) is to be sterilized or pasteurized. Each of the patterns 402, 404, 406, and 408 are different, but occlude microwave radiation no more than 1-30% from above or below the transport carrier 400. While FIG. 5B shows patterns which are different at each location, in many embodiments the patterns at each opening in the conductive layer 410 will be the same and will be optimized for the food product or other load which is being sterilized or pasteurized. Common to each of the patterns 402, 404, 406, and 408, there are members which span the opening horizontally (i.e., in the lengthwise direction of the transport carrier) and members which project at least partially vertically across the opening (i.e., in the widthwise direction of the transport carrier). These different patterns can have different member thicknesses (see 402 and 404), or different numbers of horizontal and vertical members. Each of the pattern designs can provide slightly different heating effects from each other; however, all of the pattern designs will provide more uniform heating to the underlying (or overlying) item to be sterilized or pasteurized at each location in the transport carrier than if no patterned occlusion of the opening were present.

Figure 5C:
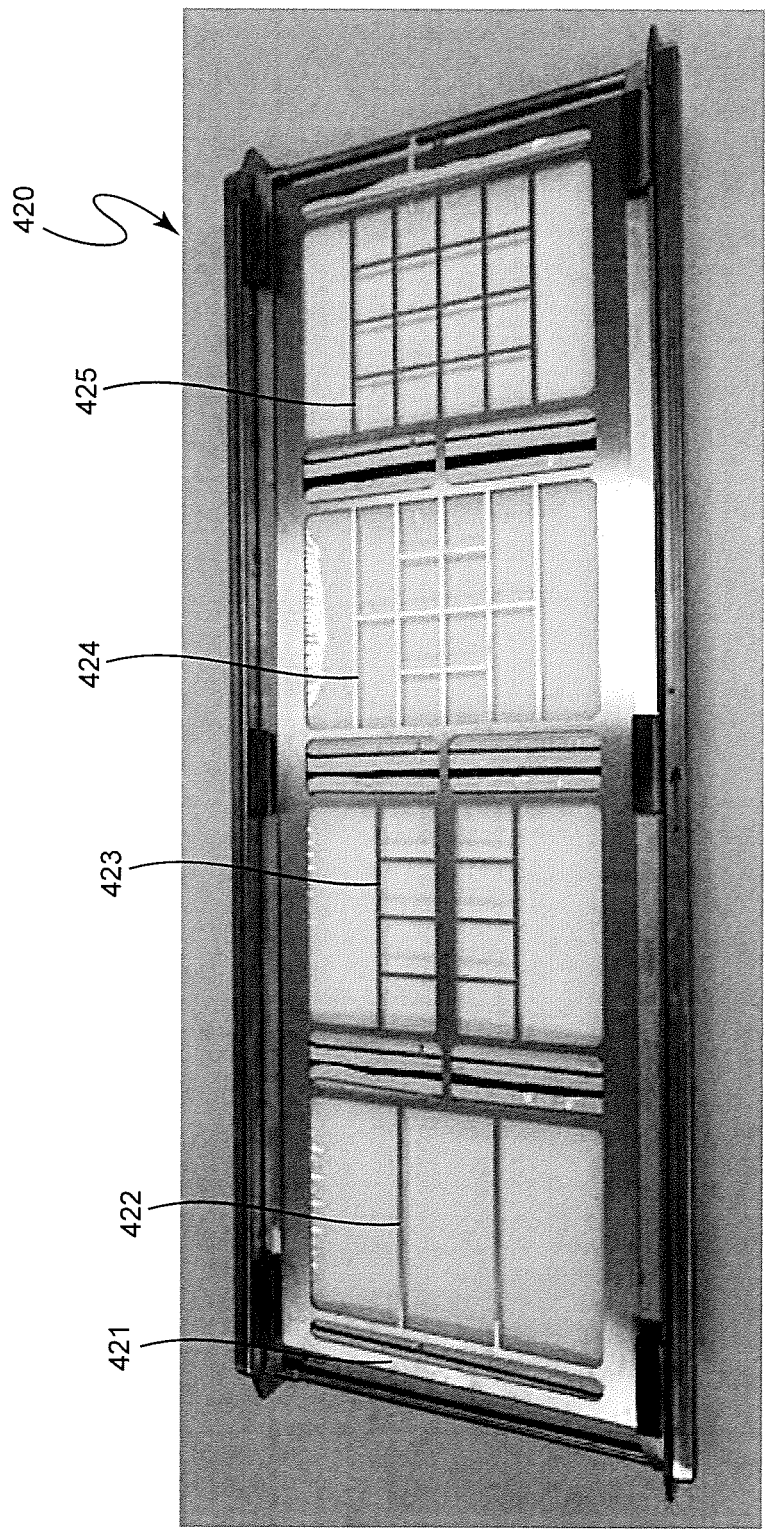
FIG. 5C is a top view of a transport carrier with different electrically conductive patterns (e.g., metal or metal alloy) at each of four locations where, for example, four 16 Oz, 20 Oz, or 30 Oz pouches or trays may be located.

FIG. 5C shows another example of a transport carrier 420 having a conductive (e.g., metal) layer 421 with different patterns 422, 423, 424, and 425 at each of four locations on the carrier 420. Each of the patterns 422, 423, 424, and 425 occlude microwave radiation no more than 1-30% from above or below the transport carrier 400. The transport carrier 420 of FIG. 5C, in contrast to the transport carrier 400 of FIG. 5B, is preferably designed to carrier 16 oz, 20 oz, or 30 Oz trays at the four locations, and may carry trays at different volumes at each of the different locations. However, as discussed previously, once the system is optimized, it is expected that the transport carrier will have a single pattern at each of the four locations and that same sized trays will be used at each of the four locations. The pattern 422 in transport carrier 420 is the only pattern which does not have any portion of the pattern extending vertically (i.e., in a direction spanning between the left and right sides of the carrier 420). Heating results with such patterns have not typically been as uniform as patterns 423, 424, and 425 where at least one or more members extend vertically across all or part of the opening for the pattern area at the area of exposure.

While FIG. 3, 5B and 5C show conductive patterns (e.g., metal or metal alloy patterns) loosely based on a Faraday cage, the patterns can be, in some applications, take the form of patterns of letters, lines, X's, or O's, and may in fact be any desired pattern including random patterns. Depending on the application, patterns at different locations may be the same or different in the same layer or series of cages. Similarly, depending on the application, the patterns may be the same or different from each other on the top and the bottom layers of the carrier. A greater percentage of electrically conductive pattern material might be used in one part of an area to be sterilized or pasteurized if, for example, heating of that part of the area is desired to proceed at a lower rate than at another part of the area. This type of pattern variation might pursued if, for example, different types of food products are stored in different parts of the same product package, and there is a desire to heat one food product more intensely than the other food product FIG. 6 demonstrates the unexpected superiority of having electrically conductive patterns or cages which partially occlude or otherwise interrupt microwave energy from a direct path to the location of items on a transport carrier, when the transport carrier is directed through a sterilization or pasteurization system as shown, for example, in FIG. 1. In the testing, items on a transport carrier were pre-heated in a fluid-filled preheating section at 30° C. for 15 min. Then, they were transported at 40 inches/minute through a fluid filled heating section at 93° C. with 100 second holds at a microwave emission station emitting 915 mHz microwaves at 5 kW and at 8.7 kW. Finally, the transport carriers were subjected to cooling in a fluid filled cooling section for 5 min at 23° C.

Figure 6:
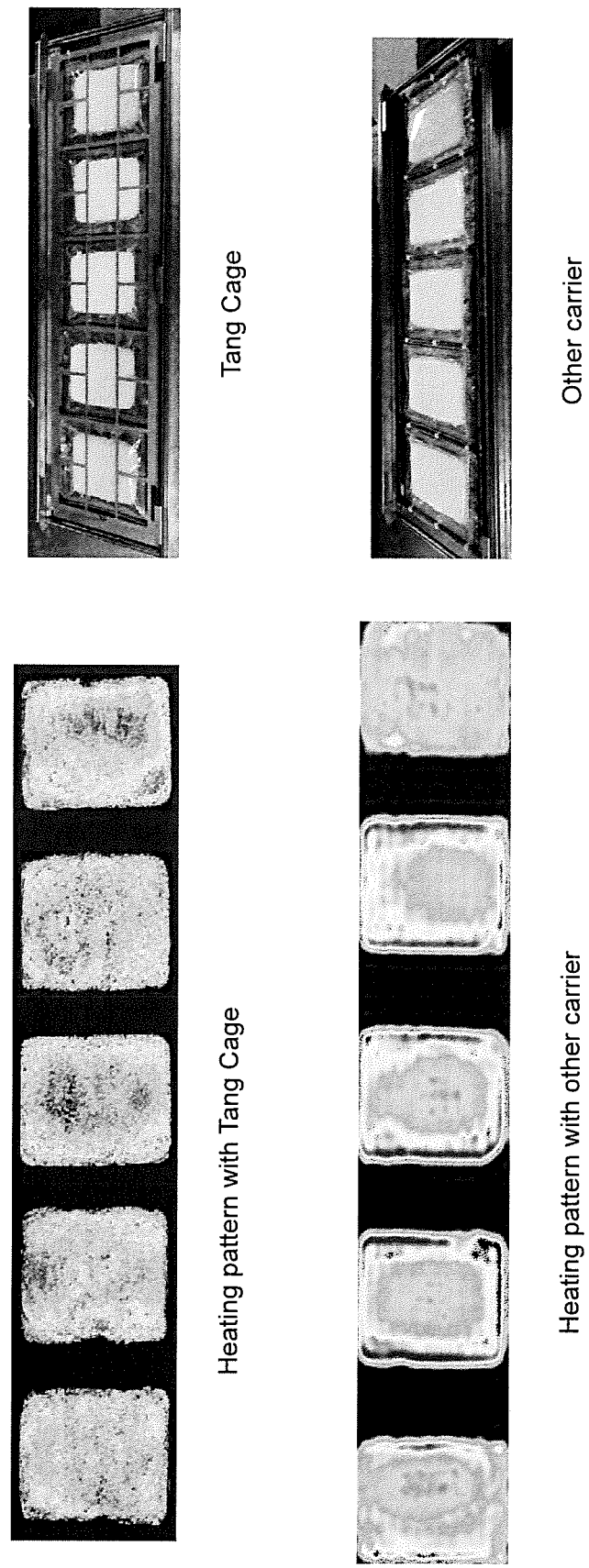
FIG. 6 shows heating pattern images of items subjected to microwave heating which were obtained using transport carriers according to the present invention and obtained using transport carriers without a patterned cage or layer as contemplated by an embodiment of the invention under the same processing conditions.

FIG. 6 shows the heating pattern observed using the chemical marker method developed by Zhang et al. (see, e.g., Zhang, W., Tang. J., Liu, F., Bohnet, S., Tang, Z., 2014. Chemical marker M2 (4-hydroxy-5-methyl-2(211)-furanone) formation in egg white gel model for heating pattern determination of microwave-assisted pasteurization processing. *Journal of Food Engineering,* 125: 69-76, and Jain. D., Wang, J., Liu, R. Tang, J., Bohnet, S. 2017. Application of non-enzymatic browning of fructose for heating pattern determination in microwave assisted thermal pasteuization system. *Journal of Food Engineering.* 210: 27-34, both of which are herein incorporated by reference) for five test model food products heated by microwave emissions as discussed above with the electrically conductive patterns above and below pouches containing the test food products. The test configuration is identified as a Tang Cage and resembles the carrier design shown in FIG. 3. As can be seen from FIG. 6, with the Tang Cage, the heating pattern for each of the pouches is fairly uniform with limited numbers of hot spots or cold spots. In contrast, when a carrier without an occluding electrically conductive layer (identified in FIG. 6 as "Other carrier") transported five identical test foods through the sterilization or pasteurization system under the same heating and microwave exposure conditions as discussed above, FIG. 6 shows that the test foods had considerably more variation (i.e., non-uniformity) in terms of heating with more hot spots and cold spots than occurred with the Tang Cage.

Thus, the present invention contemplates placing a small amount of electrically conductive material, e.g., a pattern of metal or metal alloy, directly in front of the food product or other item to be sterilized or pasteurized. Due to the occlusion and use of conductive material, one of ordinary skill in the art would expect this to disrupt or adversely affect the uniformity of heating to the underlying item. However, the test results in FIG. 6 demonstrate exactly the opposite result. That is, with the Tang Cage better uniformity of heating was obtained throughout the heated object, and without the Tang Cage the test food products showed more variation in heating patterns throughout the food products. Thus, the invention provides for superior results when sterilizing or pasteurizing items transported through a sterilization or pasteurization system on transport carriers, particularly all metal or metal alloy transport carriers.

Figure 7:
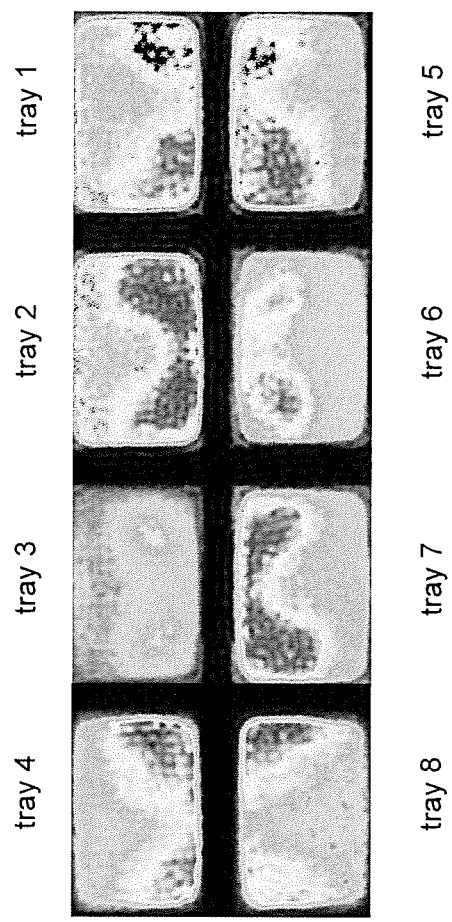
FIG. 7 shows a transport carrier with eight 10.5 Oz trays without a metal shielding pattern above and below each of the trays results in a fairly non-uniform heating pattern when subjected to heating in a system as described in FIG. 1.
Figure 7:
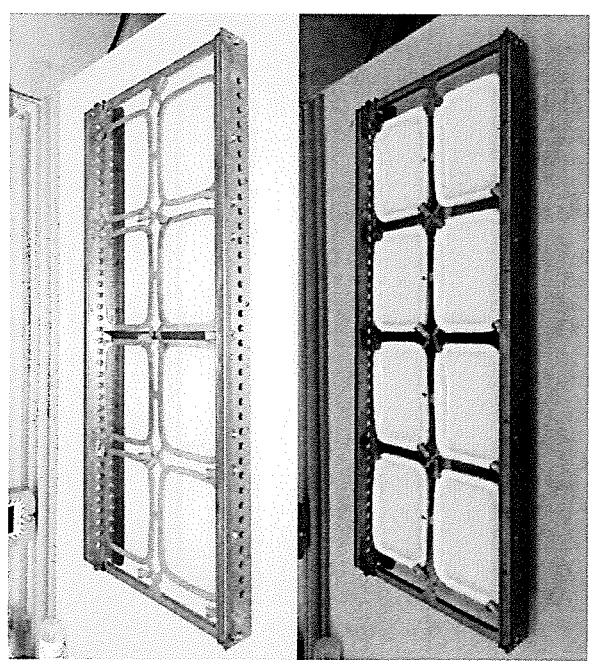
Figure 8:
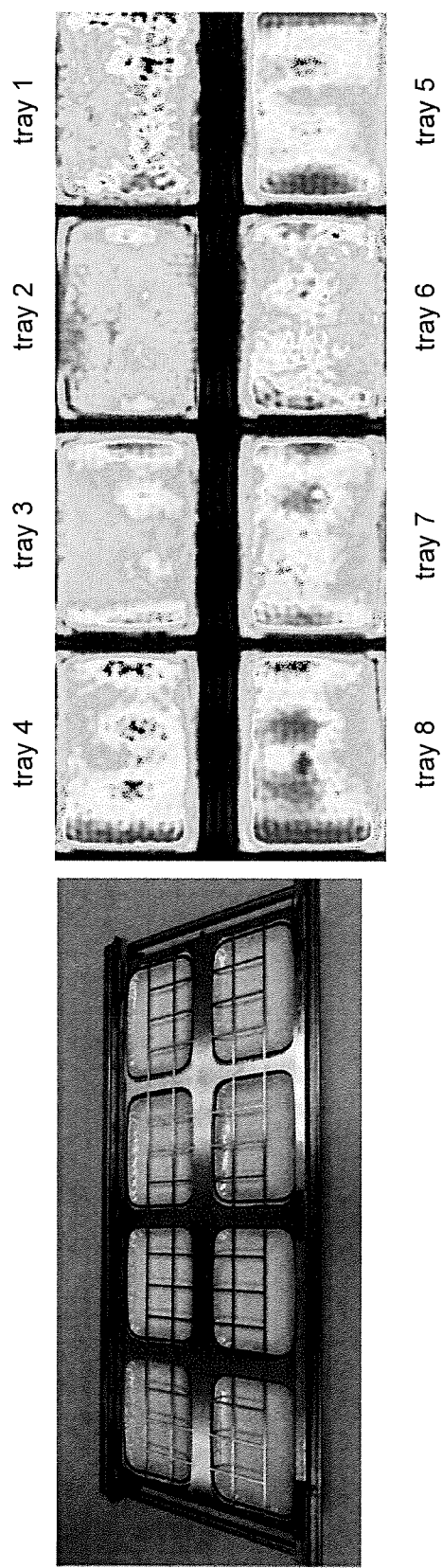
FIG. 8 shows a transport carrier, set up and handled identically to the transport carrier of FIG. 7, except that it includes metal shielding patterns above and below each of the trays and results in a much more uniform heating pattern when subjected to heating in a system as described in FIG. 1 under substantially similar conditions to those for FIG. 7.

FIGS. 7 and 8 show further examples of improved comparative results of the invention. Specifically, FIG. 7 shows that in a transport carrier holding eight 10.5 Oz model foods without an overlaying and underlying electrically conductive pattern (e.g., metal or metal alloy) at each of the eight locations of the 10.5 Oz trays, the heating pattern was not uniform and tended to overheat the edges of the model foods towards the center longitudinal line of the transport carrier when it is passed through a system as shown in FIG. 1 under conditions similar to those discussed above for FIG. 6. By contrast, in FIG. 8 where an overlying and underlying pattern of electrically conductive material was employed at each of the eight locations of the 10.5 Oz model foods the heating pattern was far more uniform and did not have an overheating tendency towards the center longitudinal line of the transport carrier.

Figure 9A:
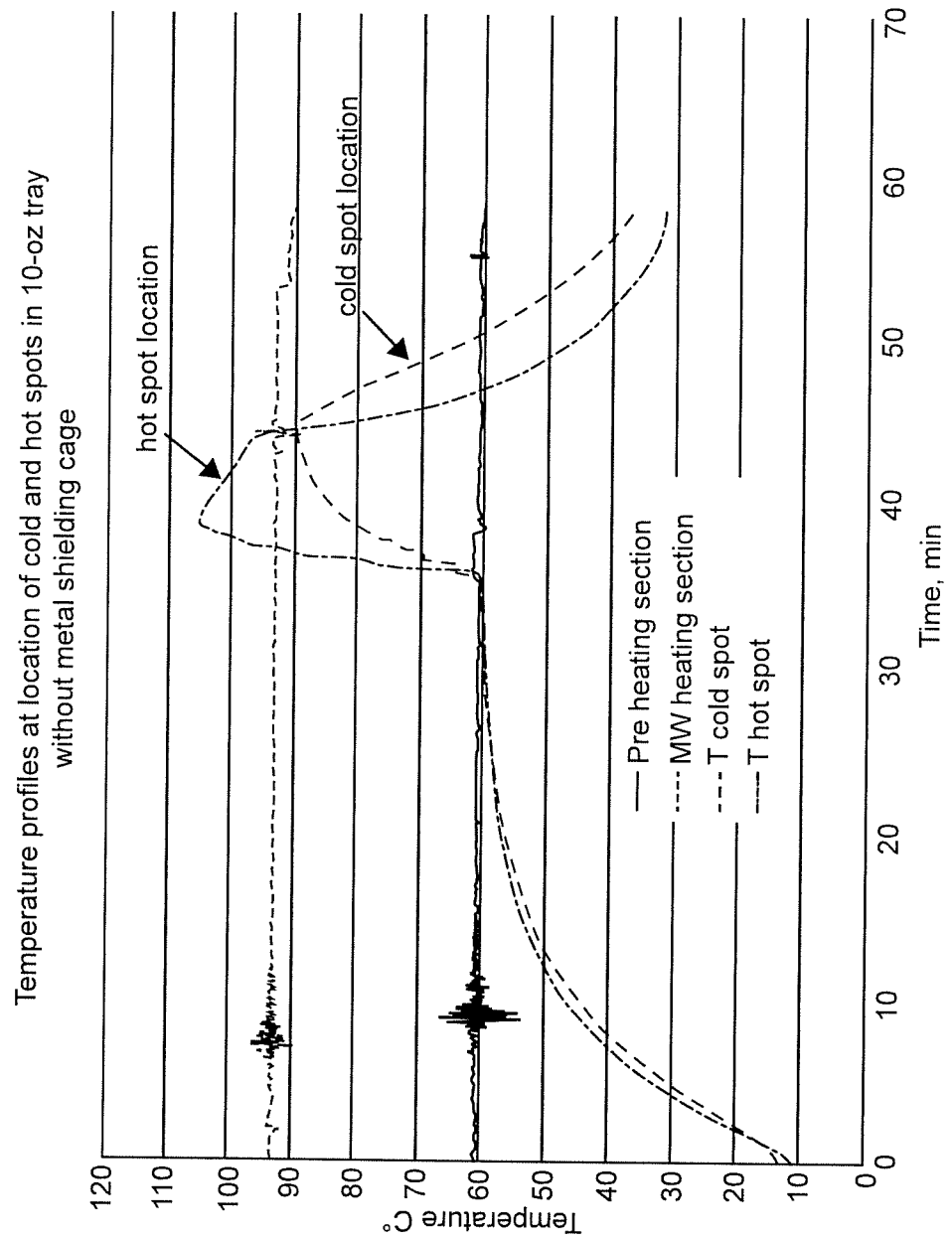
FIG. 9A-B are graphs showing the temperature differences between hot spots and cold spots in model foods processed with carriers as shown in FIGS. 7 and 8, and respectively shows substantially better results (e.g., a reduction of 60% or more in the temperature differential between hot and cold spots) when a metal pattern is employed as shown in FIG. 8 compared to a when no metal pattern is present as shown in FIG. 7.
Figure 9B:
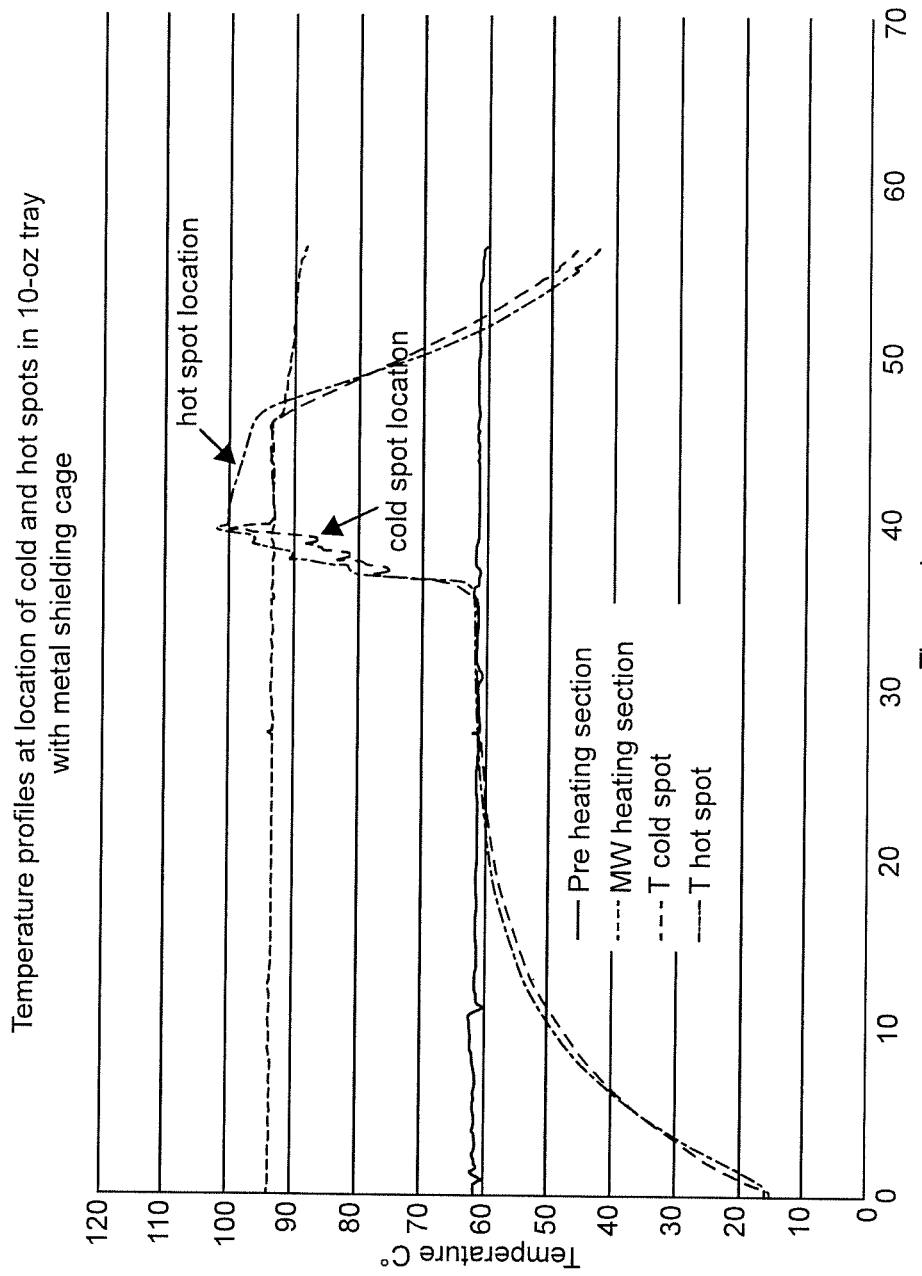

FIGS. 9A and 9B show the temperatures of the hot spot and cold spot locations from model foods that were sent through a system as shown in FIG. 1 without the metal shielding cage (as shown in FIG. 7) and with the metal shielding cage (as shown in FIG. 8), respectively. It can be seen that when the metal shielding cage (as shown in FIG. 8) is present the differential between cold spot and hot spot temperatures found in the food is reduced by at least 60% and preferably by 75% or more.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. It is to be noted that as used herein, the term "adjacent" does not require immediate adjacency. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

We claim:

1. A transport carrier for carrying one or more items to be sterilized or pasteurized by microwave emissions, comprising:

a carrier base transportable through a fluid filled microwave heating zone,
the carrier base having opposing first and second sides and opposing first and second ends, the opposing first and second sides and the first and second ends defining a space in the carrier base where one or a plurality of items to be sterilized or pasteurized are positionable at one or a plurality of locations within the space,
the carrier base having a top and a bottom, and the space in the carrier base where the one or the plurality of items to be sterilized or pasteurized are positionable is configured to be exposed from either or both the top and the bottom of the carrier base so as to allow microwave emissions to contact or penetrate the one or the plurality of items to be positioned in the space from above and/or below the carrier base,
each of the one or the plurality of locations defining an area of exposure from above and/or below the carrier base to microwave emissions for the one or the plurality of items to be positioned at the one or the plurality of locations; and one or more patterned electrically conductive cages or layers configured to fit within the space defined by the opposing first and second sides and the first and second ends of the carrier base and either or both under and over the one or the plurality of items to be positioned at the one or the plurality of locations within the space, the one more patterned electrically conductive cages or layers being sized so as to interrupt microwave emissions emitted directly from one or more microwave emission sources above and/or below the carrier base over 1-30% of the area of exposure defined by each of the one or the plurality of locations, wherein the electrically conductive cages or layers comprise or are comprised of metal or metal alloy material, and wherein the carrier base comprises or is comprised of metal or metal alloy material.

2. The transport carrier of claim 1 wherein the one or the plurality of locations in the space includes three or more locations.

3. The transport carrier of claim 1 wherein the one or the plurality of locations in the space includes six or more locations.

4. The transport carrier of claim 2 wherein at least two of the plurality of locations define different sized areas and are configured to accommodate different sized items.

5. The transport carrier of claim 2 further comprising one or more walls separating individual locations from other locations in the plurality of locations, wherein said one or more walls comprise or are comprised of metal or metal alloy material.

6. The transport carrier of claim 2 wherein the one or more patterned electrically conductive cages or layers comprise at least a first layer having separate, spaced apart, pattern areas for each location of the plurality of locations.

7. The transport carrier of claim 6 wherein the one or more patterned electrically conductive gates or layers comprises a second layer having separate, spaced apart, pattern areas for each location of the plurality of locations.

8. The transport carrier of claim 7 wherein the first layer and the second layer are spaced apart vertically in a top to bottom dimension of the carrier base by a distance configured to accommodate the plurality of items to be sterilized or pasteurized therebetween.

9. The transport carrier of claim 7 wherein the first layer and the second layer have the same pattern configuration for the separate, spaced apart, pattern areas.

10. The transport carrier of claim 6 wherein the separate, spaced apart, pattern areas for either or both the first layer and the second layer each included one or more members which extend horizontally across an opening for the pattern area at the area of exposure and at least one or more members which extend vertically across all or part of the opening for the pattern area at the area of exposure.

11. The transport carrier of claim 1 wherein the one or more patterned electrically conductive cages or layers being are sized so as to interrupt microwave emissions emitted directly from one or more microwave emission sources above and/or below the carrier base over 3-15% of the area of exposure defined by each of the one or the plurality of locations.

12. The transport carrier of claim 1 wherein the one or more patterned electrically conductive cages or layers are affixed to a frame, and the frame is secured to at least one of the opposing first and second sides and/or opposing first and second ends.

13. The transport carrier of claim 1 wherein the one or more patterned electrically conductive cages or layers are configured to reduce a temperature differential between a hot spot and a cold spot in the one or the plurality of items to be sterilized or pasteurized by at least 60% compared to that which can be achieved with an identical transport carrier without the one or more patterned electrically conductive cages or layers.

14. A transport carrier for carrying one or more items to be sterilized or pasteurized by microwave emissions, comprising:

a carrier base transportable through a fluid filled microwave heating zone, the carrier base having opposing first and second sides and opposing first and second ends, the opposing first and second sides and the first and second ends defining a space in the carrier base where a plurality of items to be sterilized or pasteurized are positionable at a plurality of locations within the space, the carrier base having a top and a bottom, and the space in the carrier base where the plurality of items to be sterilized or pasteurized are positionable is configured to be exposed from both the top and the bottom of the carrier base so as to allow microwave emissions to contact or penetrate the plurality of items to be positioned in the space from above and below the carrier base, each of the one or the plurality of locations defining an area of exposure from above and below the carrier base to microwave emissions for the plurality of items to be positioned at the plurality of locations; and top and bottom patterned electrically conductive layers configured to fit within the space defined by the opposing first and second sides and the first and second ends of the carrier base, wherein the top and bottom patterned electrically conductive layers are spaced apart vertically in a top to bottom dimension of the carrier base by a distance configured to accommodate the plurality of items to be sterilized or pasteurized therebetween, wherein the top and bottom electrically conductive layers being sized so as to interrupt microwave emissions emitted directly from one or more microwave emission sources above and below the carrier base over 1-30% of the area of exposure defined by each of the plurality of locations, wherein the top and bottom electrically conductive layers each have separate, spaced apart, pattern areas for each location of the plurality of locations.

15. The transport carrier of claim 14 further comprising slots or flanges of the opposing first and second sides of the carrier base for guiding and holding the top and bottom patterned electrically conductive layers.

16. The transport carrier of claim 14 further comprising electrically conductive straps or plates separating individual locations of the plurality of locations from each other.

17. The transport carrier of claim 14 wherein the top and bottom patterned electrically conductive layers, the carrier base, and the electrically conductive straps or plats comprise or are comprised of metal or metal alloy material.

18. The transport carrier of claim 14 wherein the top and bottom electrically conductive layers are configured to reduce a temperature differential between a hot spot and a cold spot in the one or the plurality of items to be sterilized or pasteurized by at least 60% compared to that which can be achieved with an identical transport carrier without the top and bottom electrically conductive layers.

\* \* \* \* \*